United States Patent
Pierre et al.

(10) Patent No.: US 8,172,890 B2
(45) Date of Patent: May 8, 2012

(54) COMBINATION UNDERBODY AND OVERBODY BLANKET

(75) Inventors: Joseph Pierre, Brockton, MA (US); Rachel Starr, Randolph, MA (US); Alan Stec, East Bridgewater, MA (US)

(73) Assignee: Smiths Medical ASD, Inc., Rockland, MA (US)

(*) Notice: Subject to any disclaimer, the term of this patent is extended or adjusted under 35 U.S.C. 154(b) by 613 days.

(21) Appl. No.: 12/379,260

(22) Filed: Feb. 18, 2009
(Under 37 CFR 1.47)

(65) Prior Publication Data

US 2010/0211139 A1    Aug. 19, 2010

(51) Int. Cl.
*A61F 7/00* (2006.01)
(52) U.S. Cl. .................................................. 607/108
(58) Field of Classification Search ............ 62/259.3; 2/2.5, 81, 102, 458, 459; 607/108, 107
See application file for complete search history.

(56) References Cited

U.S. PATENT DOCUMENTS

| | | | |
|---|---|---|---|
| 5,072,455 A * | 12/1991 | St. Ours | 2/81 |
| 5,735,890 A | 4/1998 | Kappel et al. | |
| 5,773,275 A | 6/1998 | Anderson et al. | |
| 5,839,133 A | 11/1998 | Dickerhoff et al. | |
| 7,716,940 B2 * | 5/2010 | Farnworth et al. | 62/259.3 |
| 7,762,096 B2 * | 7/2010 | Fuchs | 62/259.3 |
| 2008/0027522 A1 | 1/2008 | Bieberich | |
| 2009/0248120 A1 | 10/2009 | Starr et al. | |

OTHER PUBLICATIONS

PCT International Search Report and Written Opinion, ISA/KR, Oct. 7, 2010.

* cited by examiner

*Primary Examiner* — Manuel Mendez
(74) *Attorney, Agent, or Firm* — Louis Woo

(57) ABSTRACT

A combination underbody and overbody blanket has first and second portions sandwiching a middle portion. The first portion may be shorter than the second portion. An opening is provided at the middle portion, or at a location that overlaps the middle and first portions. The opening has a dimension sufficiently large to enable the head of a patient to pass through. At least one air inlet is provided at the middle portion to allow air to be input into the blanket. The blanket is configured in the shape of a poncho, with the first portion covering the front torso of the patient and the second portion covering the back of the patient. A tearable seal is provided at the first portion that allows the first portion to be separated into two halves to expose the front upper torso of the patient and/or to facilitate the placement of the middle portion about the neck and onto the shoulders of the patient.

19 Claims, 4 Drawing Sheets

COMBINATION UNDERBODY AND OVERBODY BLANKET

FIELD OF THE INVENTION

The present invention relates to convective warming blankets, and more particularly relates to a combination underbody and overbody blanket that may be configured into the shape of a poncho.

BACKGROUND OF THE INVENTION

There is disclosed in U.S. Pat. No. 5,674,269 an inflatable tube covered by a deformable resilient access panel that covers the patient. The underside of the patient however rests on the bed or table. There is also disclosed in the prior art (U.S. Pat. Nos. 5,697,963, 5,800,489 and 7,001,416) a thermal blanket for use by a patient sitting on a chair. The blanket has an opening through which the head of the patient passes. The blanket is positioned in front of the patient for warming the front of the patient. These types of thermal blankets do not provide any warming to the back of the patient. There are further disclosed a number of garments worn by patients that have heating sections inside the garments. Such garments are disclosed in U.S. publications 2005/0143796, 2006/0184217, 2006/0184218, 2007/0093882, 2007/0093884 and 2007/0093885. There currently is no convective warming blanket in the market that covers both the front and the back of a patient.

SUMMARY OF THE PRESENT INVENTION

The convective warming blankets of the present invention is a combination underbody and overbody blanket, with the underbody portion being longer than the upper body portion. In particular, the blanket has one portion and an other portion that sandwich a middle portion. The one and other portions are foldable substantially orthogonal to the middle portion along the same direction so that the blanket has a configuration in the form of a poncho. The one and other portions may also be referred to as the first and second portions, or the front and back portions of the blanket.

As is conventionally known, the blanket is made up of two sheets of air impermeable layers that are sealingly bonded at their respective peripheries and at other different locations so that temperature treated air, for example heated air, may be input into the blanket for inflating the same. For the present invention blanket, an opening is provided at substantially the middle portion, although it may overlap to the one or the other portion. There is provided an air inlet port at either side of the opening at the middle section so that, when in operation, either one of the inlet port may be used to connect to an air hose from an air conditioning unit, for example an air warmer, to pump in temperature treated air to inflate the blanket.

To facilitate the folding or bending of the one and other portions relative to the middle portion of the blanket, at least two sets of in alignment spaced apart seals orthogonal to the length or longitudinal axis of the blanket are provided at the middle section so that the one portion is bendable or foldable relative to the middle portion by way of the first set of in alignment seals while the second portion is bendable or foldable relative to the middle portion by way of the second set of in alignment seals. The one and other portions are folded in the same direction relative to the middle portion so that in its natural configuration when fully inflated, the combination underbody and upper body blanket of the present invention would be configured in the shape of an upside-down U, with one leg of the U being shorter than the other. In other words, the convective warming blanket of the present invention is configured in the shape of a poncho blanket—preferably with the shorter portion covering the front of the patient, the longer portion covering the back of the patient, and the middle section positioned at or on the shoulders of the patient, as the patient's head is passed through the opening at the middle portion. The layer of the blanket that is in contact with the patient has a plurality of apertures that enable the temperature treated air, for example heated air, in the blanket to output towards the patient.

There is a frangible or tearable seal or stripe that extends from the proximal end of the blanket that defines the one end of the front portion that covers the front of the patient to the opening at the middle portion of the blanket. The frangible seal enables the front portion of the blanket to be separated into two parts or halves so that the blanket may be fitted over the head of the patient if the patient happens to be intubated, or if there is some attachment to the head of the patient that prevents the head of the patient from passing through the opening. Also, the frangible stripe allows the front portion of the blanket to be separated to expose the front upper torso of the patient.

The present invention therefore relates to a combination upper body and under body convective blanket that comprises an inflatable structure having one portion and other portion separated by a middle portion configured to enable the one portion and the other portion to be folded relative to the middle portion so that both the one and other portions extend substantially orthogonally from the middle portion in the same direction. The blanket further includes an opening provided at or overlapping the middle portion having a dimension sufficient to enable the head of a patient to pass through so that the middle portion of the blanket is substantially positioned relative to the shoulders of the patient and the one portion of the blanket is positioned to the front of the patient while the other portion of the blanket is positioned to the back of the patient.

The present invention also relates to a blanket for warming a patient that comprises an inflatable structure having a first horizontal end and a second horizontal end defining the longitudinal length of the structure and a first vertical end and a second vertical end defining the width of the structure. The blanket has one and other portions sandwiching a middle portion, the one and other portions foldable relative to the middle portion in the same direction substantially orthogonal to the middle portion. An opening is provided in the structure substantially midway between the vertical ends at substantially the middle portion. The opening has a dimension sufficiently large to a enable the head of the patient to pass through so that when the structure is placed on the patient with the head of the patient extending through the opening and the one and other portions folded relative to the middle portion, the one portion of the structure covers at least a part of the front of the body of the patient and the other portion of the structure covers at least a part of the back of the body of the patient.

The present invention moreover relates to a convective warming blanket that has one and other portions fluidly interconnected by and sandwiching a middle portion. The one and other portions are foldable substantially orthogonal relative to the middle portion in the same direction. An opening is provided substantially at the middle portion so that when the blanket is placed over the patient with the head of the patient passing through the opening and the one and other portions folded over in the same direction, the blanket is configured into the shape of a poncho with the middle portion positioned substantially on or at the shoulders of the patient and the one and other portions covering at least corresponding parts of the front and back, respectively, of the body of the patient.

BRIEF DESCRIPTION OF THE FIGURES

The present invention will become apparent and the invention itself will be best understood by reference to the following description of the invention taken in conjunction with the following drawings, wherein.

DETAILED DESCRIPTION OF THE INVENTION

Figure 1:
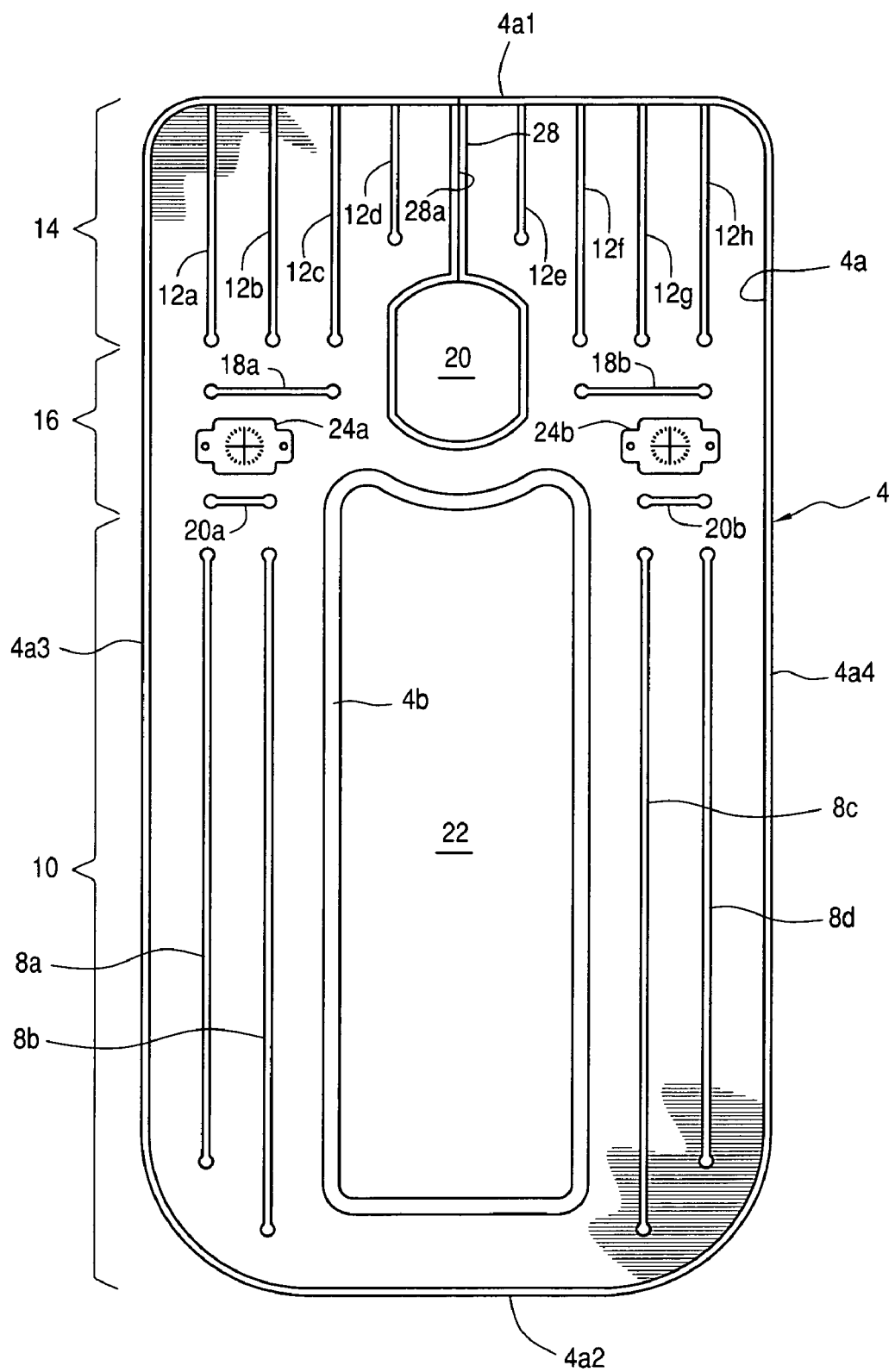
FIG. 1 is a plan view of the top layer of the blanket of the present invention with the blanket being fully extended without any folding or bending.
Figure 2:
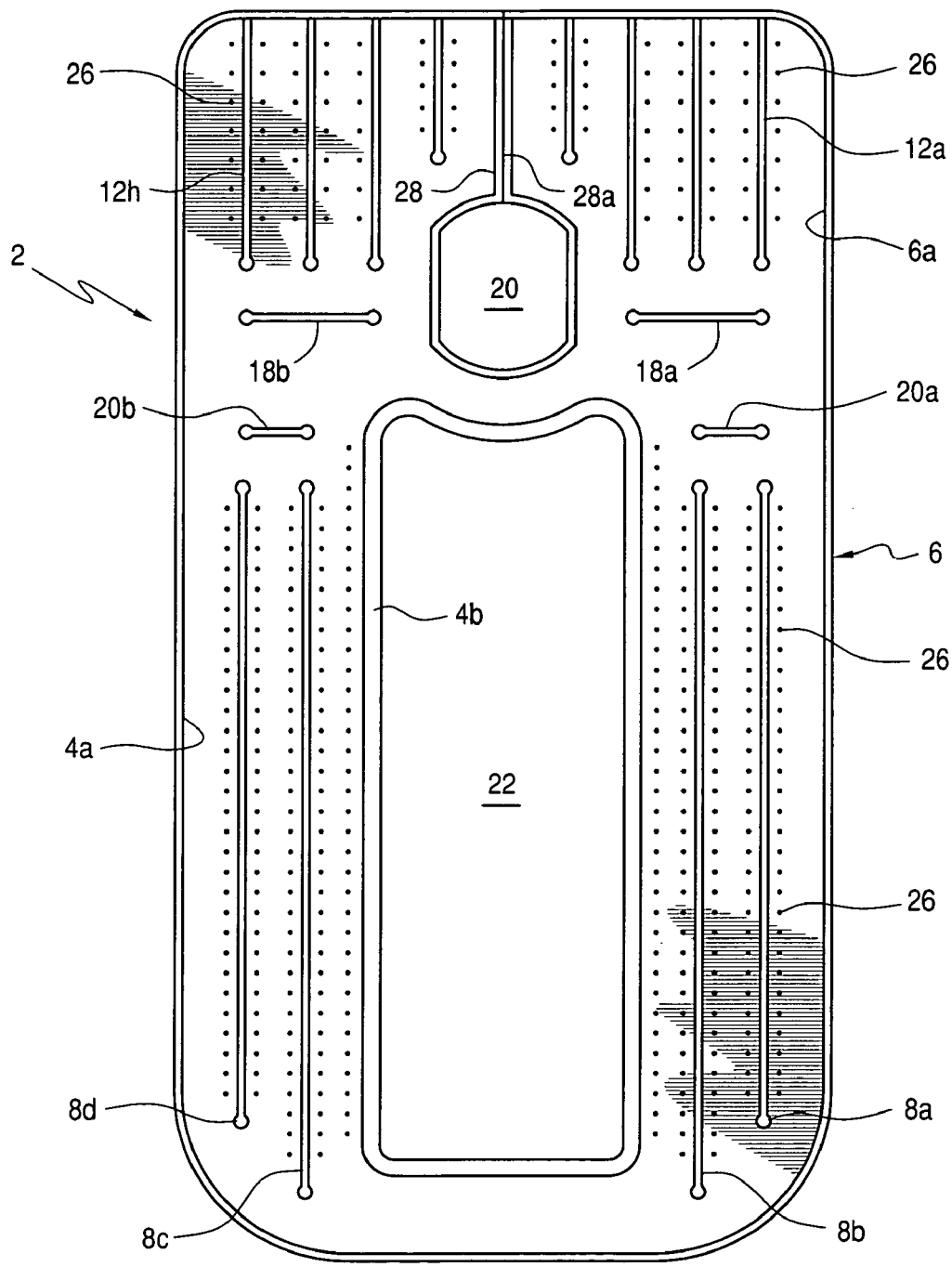
FIG. 2 is the plan view of the bottom layer of the blanket of the present invention that comes into contact with the patient.

With reference to FIGS. 1 and 2, the combination upper body and lower body convective warming blanket 2 of the present invention is shown to have an upper layer or sheet 4 and a lower or bottom layer sheet 6. The air impermeable upper and lower sheets 4 and 6 are sealingly bonded at their respective peripheries 4a and 6a, and other different locations by means of other seals such as longitudinal seals 8a-8d for the major portion 10 of blanket 2, and longitudinal seals 12a-12h for the smaller minor portion 14 of the blanket. Sandwiched between portions 10 and 14 is a middle portion 16 that includes a plurality of seals 18a, 18b, 20a and 20b that extend orthogonally relative to the horizontal seals 8a-8d and 12a-12h. For ease of discussion, seals 18a, 18b and 20a, 20b may be referred to horizontal seals, while seals 8a-8d and 12a-12h may be referred to as vertical seals. Although designated as separate portions 14, 16 and 10, it should be appreciated that there is overlapping among the portions, for example the overlapping between upper portion 14 and middle portion 16, and the overlapping between middle portion 16 and major portion 10. It is at the middle portion 16 that horizontal seals 18a, 18b and 20a and 20b are located.

For the present invention blanket, portion 14 may be referred to as the front portion while portion 10 may be referred to as the back portion, as those portions are meant to cover the front and back, respectively, of a patient. The front portion 14, middle portion 16 and back portion 10 are confined by the horizontal proximal end 4a1 and the horizontal distal end 4a2 of the blanket. Width-wise the blanket is defined by the peripheral seals 4, 6 at vertical ends 4a3 and 4a4.

There is provided in blanket 2 an opening 20 at an overlap area of portions 14 and 16. For discussion purposes and the for the sake of simplicity, opening 20 may be considered to be at the middle portion 16, or substantially at middle portion 16. There is provided at portion 10 of blanket 2 a non-inflatable section 22 that is sealingly bonded by an internal seal 4b.

Further provided at blanket 2, more specifically at middle portion 16 between the sets of horizontal in alignment spaced apart seals 18a, 18b and 20a, 20b, are air inlet ports 24a and 24b. During operation, only one of the air inlet ports 24a and 24b is used for connecting to an air hose 25, shown in FIG. 4, which in turn is connected to an air conditioning unit such as an air warmer or heater, not shown, so that temperature treated air, for example heated air, is input to the blanket for inflating the same.

A plurality of apertures 26 are provided at the lower sheet 6 so that the air input to blanket 2 is output from the blanket towards the patient. As shown in FIG. 2, respective row(s) of spaced apertures 26 are provided adjacent to each of the longitudinal seals 8a-8d and 12a-12h.

A stripe in the form of a frangible or tearable seal 28 that has a plurality of slits or perforations 28a along its length extends from proximal end 4a1 through the front portion 14 to opening 20. When an appropriate force is applied thereto, seal 28 is torn along its length so that front portion 14 is separated into two parts or halves, per shown in FIG. 4.

Although shown in an extended horizontal form, blanket 2, when properly inflated, has a natural configuration of an upside-down U, with one leg of the blanket, i.e., the front portion 14, being shorter than the other leg, i.e., the back portion 10. Front portion 14 and back portion 10 are foldable in the same direction substantially orthogonal relative to middle portion 16, so that the bottom sheet 6 shown in FIG. 2 would be in contact with both the front and the back of the patient, per shown in FIG. 3.

Figure 3:
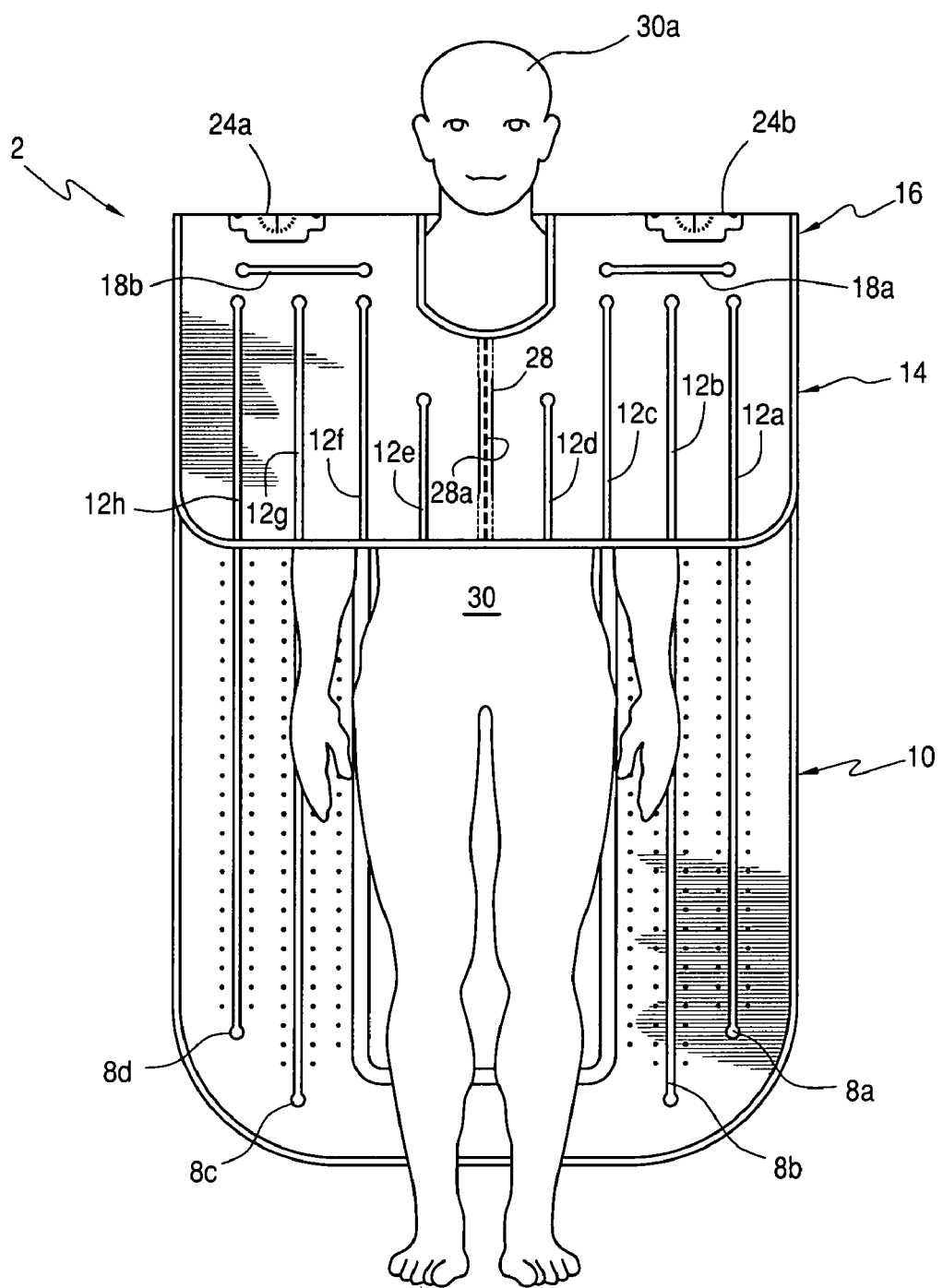
FIG. 3 is an exemplar view of the blanket of the present invention with its front and back portions having been folded orthogonally relative to the middle portion so that the front portion of the blanket covers the front torso of the patient and the back portion of the blanket covers the back of the patient.

With reference to FIG. 3, a patient 30 is shown to be covered by blanket 2, which is shown to have a configuration in the shape of a poncho. As shown, front portion 14 covers the front torso of patient 30, with the patient's head 30a extending from opening 20 of blanket 2. As discussed earlier, the middle portion 16 of the blanket is shown to be positioned on or at the shoulders of patient 30, with the air inlet ports 24a and 24b located thereat.

Figure 4:
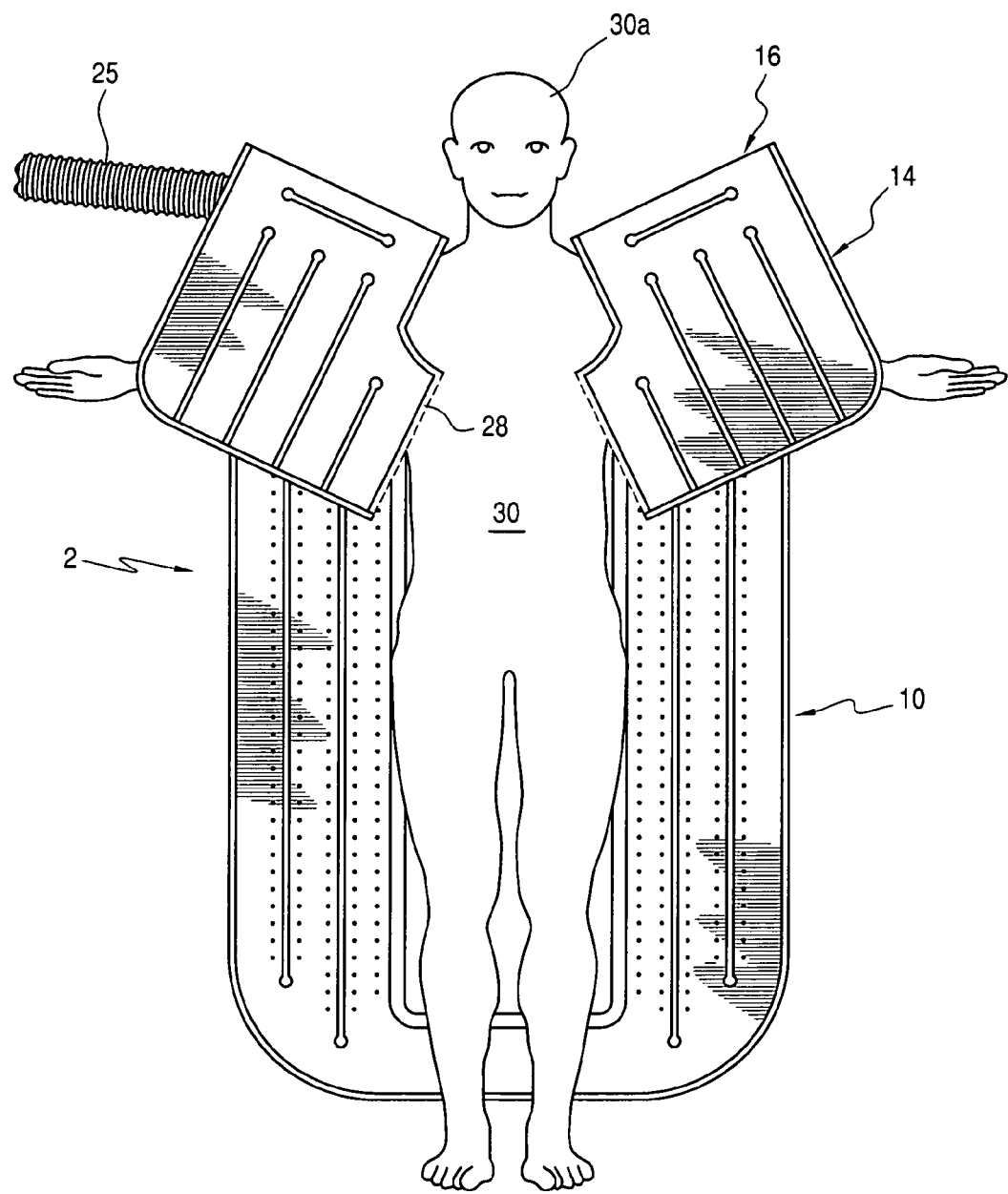
FIG. 4 shows the front portion of the inflated blanket having been separated into two half sections to expose the front upper torso of the patient.

With the blanket in the inflated state shown in FIG. 4, the horizontal seals 18a, 18b and 20a, 20b (not shown) assist in the folding of front and back portions 14 and 10 relative to middle portion 16. With the blanket inflated, temperature treated air is output from both back portion 10 and front portion 14 to the back and front, respectively, of the patient to warm the patient. Further with respect to FIG. 4, frangible seal 28 is shown to have been separated so that front portion 14 is parted into two halves to expose the front upper torso of the patient and also possibly to gain access to an intubated patient, as each or both of the halves may be flipped or folded back so as to extend co-planarly with the rest of the blanket per shown in FIG. 2. Also, by being able to be separated into two parts, front portion 14 may be readily placed over the head 30a of the patient, if the patient happens to be intubated or if there is some other attachment to the head of the patient that otherwise would have prevented the head 30a of the patient to pass through opening 20 of the blanket.

With the combination underbody and overbody blanket of the present invention, the patient may lie on the back portion 10 while his front torso is being covered by the front portion 14. Alternatively, blanket 2 may be used to provide a constant source of heat to the patient in those instances where the patient is standing or sitting. With the addition of adhesive means, such as for example tape or Velcro at frangible seal 28, after having been separated into halves, front portion 14 may be reattached as one piece by means of the adhesive at frangible slit 28. Although described as the front and back portions, portions 14 and 10 may also be referred to as the first or second portion, or the one and other portions.

The invention disclosed above is subject to many variations, modifications and changes in detail. Thus, it is intended that all matters described throughout this specification and shown in the accompanying drawings be interpreted as illustrative only and not in a limiting sense. Accordingly, it is intended the invention be limited only by the spirit and scope of the hereto appended claims.

The invention claimed is:

1. A combination overbody and underbody convective blanket comprising: two sheets sealingly bonded to each other at their respective peripheries and at other locations to form an inflatable structure having one portion and other portion separated by a middle portion configured to enable the one portion and the other portion to be folded relative to the middle portion so that both the one and other portions extend substantially orthogonal from the middle portion in the same direction, an opening provided at or overlapping the middle portion having a dimension sufficient to enable the head of a patient to pass through so that the middle portion of the blanket is substantially positioned relative to the shoulders of the patient and the one portion of the blanket is positioned to the front of the patient while the other portion of the blanket is positioned to the back of the patient, a plurality of apertures formed on the sheet in contact with the patient for outputting air input to inflate the structure to the patient.

2. Blanket of claim 1, wherein the blanket has a first end and a second end, the one, other and middle portions of the blanket confined longitudinally between the first and second ends, wherein the first end defines the end of the one portion and the second end defines the end of the other portion, and wherein the blanket comprises a frangible strip extending from the first end to the opening longitudinally along the one portion so that the one portion is separable into two parts.

3. Blanket of claim 1, further comprising at least one air inlet provided at the middle portion to accept air input to the blanket at the middle portion and from there passes to the one and other portions to inflate the blanket.

4. Blanket of claim 1, wherein the other portion comprises a non-inflatable section adapted to receive the body of the patient when the patient lies onto the blanket, the other portion supporting the back of the patient while the one portion adaptable to be folded relative to the middle portion to cover at least a part of the frontal upper body of the patient.

5. Blanket of claim 1, wherein the plurality of apertures in the sheet in contact with the patient output heated air to warm both the front and back of the patient when the one and other portions are positioned substantially orthogonal to the middle portion to cover at least corresponding parts of the front and the back, respectively, of the patient.

6. Blanket of claim 1, further comprising a plurality of seals extending horizontally along the middle portion to facilitate the folding of the one and other portions relative to the middle portion.

7. Blanket of claim 6, wherein the plurality of seals comprise at least two sets of seals spaced from each other sandwiching the air inlet, each of the sets of seals having two in alignment seals one on each side of the opening to enable the one and other portions to be more readily foldable relative to the middle portion along the two sets of seals.

8. Blanket of claim 1, wherein the one and other portions each have a plurality of longitudinal seals to guide the flow of air longitudinally along the length of the one and other portions.

9. Blanket for warming a patient, comprising an inflatable structure formed by two sheets sealingly bonded to each other at their respective peripheries and at other locations, the structure formed to have first horizontal end and second horizontal end defining the longitudinal length of the structure and first vertical end and second vertical end defining the width of the structure, the blanket having one and other portions sandwiching a middle portion, the one and other portions foldable relative to the middle portion in the same direction substantially orthogonal to the middle portion, an opening provided in the structure substantially midway between the vertical ends at substantially the middle portion having a dimension sufficiently large to enable the head of a patient to pass therethrough so that when the structure is placed on the patient with the head of the patient extending through the opening and the one and other portions folded relative to the middle portion, the one portion of the structure covers at least a part of the front of the body of the patient and the other portion of the structure covers at least a part of the back of the body of the patient, a plurality of apertures formed on the sheet in contact with the patient for outputting air input to inflate the structure to the patient.

10. Blanket of claim 9, further comprising a frangible strip extending from the first horizontal end to the opening longitudinally along the one portion so that the one portion is separable into two parts.

11. Blanket of claim 9, further comprising at least one air inlet provided at the middle portion to accept air input to the blanket at the middle portion and from there passes to the one and other portions to inflate the blanket.

12. Blanket of claim 9, wherein the other portion comprises a non-inflatable section adapted to receive the body of the patient when the patient lies onto the blanket, the other portion supporting the back of the patient while the one portion adaptable to be folded relative to the middle portion to cover at least a frontal part of the upper body of the patient.

13. Blanket of claim 9, wherein the plurality of apertures output heated air to warm both the front and back of the body of the patient when the one and other portions are positioned substantially orthogonal to the middle portion to cover at least corresponding parts of the front and the back, respectively, of the body of the patient.

14. Blanket of claim 9, further comprising a plurality of seals extending horizontally along the middle portion to facilitate the folding of the one and other portions relative to the middle portion.

15. Blanket of claim 9, wherein the plurality of seals comprise at least two sets of seals spaced from each other sandwiching the air inlet, each of the sets of seals having two in alignment seals one on each side of the opening to facilitate the folding of the one and other portions relative to the middle portion.

16. A convective blanket formed by two sheets sealingly bonded to each other at their respective peripheries and at other locations and inflated by air having one and other portions fluidly interconnected by and sandwiching a middle portion, the one and other portions foldable substantially orthogonal relative to the middle portion in the same direction, and an opening at substantially the middle portion to allow the head of a patient to pass therethrough, wherein when the blanket is placed over the patient with the head of the patient passing through the opening and the one and other portions folded in the same direction, the blanket is configured into the shape of a poncho with the middle portion positioned substantially at the shoulders of the patient and the one and other portions covering at least corresponding parts of the front and back, respectively, of the body of the patient, a plurality of apertures formed on the sheet in contact with the patient for outputting the air input to inflate the blanket to both the front and back of the patient.

17. Blanket of claim 16, wherein the blanket has a first end and a second end, the one, other and middle portions of the blanket confined longitudinally between the first and second ends, wherein the first end defines the end of the one portion and the second end defines the end of the other portion, and wherein the blanket comprises a frangible strip extending from the first end to the opening longitudinally along the one portion so that the one portion is separable into two halves to enable easier movement of the head of the patient relative to the opening and/or to expose the upper torso of the patient.

18. Blanket of claim 16, further comprising at least one air inlet provided at the middle portion to accept air input to the blanket at the middle portion and from there passes to the one and other portions to inflate the blanket.

19. Blanket of claim 16, further comprising a plurality of seals extending horizontally along the middle portion to facilitate the folding of the one and other portions relative to the middle portion.

* * * * *